(12) United States Patent
Meskimen

(10) Patent No.: US 12,303,608 B2
(45) Date of Patent: May 20, 2025

(54) SPACED APART STERILIZATION LIGHTS IN AN AIRCRAFT CABIN

(71) Applicant: Thales Avionics, Inc., Irvine, CA (US)

(72) Inventor: Samuel Colt Meskimen, Huntington Beach, CA (US)

(73) Assignee: Thales Avionics, Inc., Irvine, CA (US)

( * ) Notice: Subject to any disclaimer, the term of this patent is extended or adjusted under 35 U.S.C. 154(b) by 764 days.

(21) Appl. No.: 17/558,901

(22) Filed: Dec. 22, 2021

(65) Prior Publication Data

US 2022/0193283 A1 Jun. 23, 2022

Related U.S. Application Data

(60) Provisional application No. 63/129,918, filed on Dec. 23, 2020.

(51) Int. Cl.
| | |
|---|---|
| A61L 2/10 | (2006.01) |
| A61L 2/24 | (2006.01) |
| B60Q 3/47 | (2017.01) |
| B60Q 3/68 | (2017.01) |
| B64D 41/00 | (2006.01) |
| B64D 47/02 | (2006.01) |
| B64F 5/30 | (2017.01) |
| H02J 13/00 | (2006.01) |

(52) U.S. Cl.
CPC .................. *A61L 2/10* (2013.01); *A61L 2/24* (2013.01); *B60Q 3/47* (2017.02); *B60Q 3/68* (2017.02); *B64D 41/00* (2013.01); *B64D 47/02* (2013.01); *B64F 5/30* (2017.01); *H02J 13/00036* (2020.01); *A61L 2202/11* (2013.01); *A61L 2202/14* (2013.01); *A61L 2202/25* (2013.01); *A61L 2202/26* (2013.01); *B64D 2221/00* (2013.01); *H02J 13/00007* (2020.01); *H02J 13/00026* (2020.01)

(58) Field of Classification Search
CPC .......... A61L 2/10; A61L 2/24; A61L 2202/11; A61L 2202/14; A61L 2202/16; A61L 2202/25; B60Q 3/47; B60Q 3/68; B64D 41/00; B64D 47/02; B64F 5/30; H02J 13/00036

See application file for complete search history.

(56) References Cited

U.S. PATENT DOCUMENTS

| | | | |
|---|---|---|---|
| 2019/0030195 A1* | 1/2019 | Hatti | A61L 2/24 |
| 2020/0331611 A1* | 10/2020 | Hack | B60Q 3/47 |
| 2021/0393820 A1* | 12/2021 | Childress | B64F 5/30 |

* cited by examiner

*Primary Examiner* — Lessanework Seifu

(74) *Attorney, Agent, or Firm* — Sage Patent Group

(57) ABSTRACT

A pathogen sterilization light assembly for a vehicle cabin is provided herein and may include a plurality of sterilization lights mounted spaced apart along a cabin of the vehicle and configured to emit ultraviolet (UV) light directed toward areas within the cabin to sterilize pathogens.

25 Claims, 10 Drawing Sheets

SPACED APART STERILIZATION LIGHTS IN AN AIRCRAFT CABIN

CROSS-REFERENCE TO RELATED APPLICATIONS

This application claims the benefit of U.S. Provisional Patent Application Ser. No. 63/129,918, filed on Dec. 23, 2020, the disclosure and content of which is incorporated by reference herein in its entirety.

FIELD

The present disclosure relates to vehicle systems for passenger comfort, and more particularly, surface sterilizing systems in a vehicle.

BACKGROUND

Airline passengers transport many types of pathogens including viruses, bacteria, fungi, protozoa, and worms and into aircraft cabins where they can become attached to inflight entertainment system display control surfaces, cabin seating surfaces, trays, etc. Passengers are aware of the infection risk with pathogens on cabin surfaces which can create negative feelings towards airline travel. Airlines have responded with expensive and time-consuming efforts to wipe down cabin surfaces between flights using antiseptic chemicals. Effectiveness of such manual surface cleaning depends upon the limited time-available between flights and the diligence and training of the cleaning crew. There is a tremendous need for innovation that will provide a healthier travel environment within airplane cabins.

SUMMARY

Various embodiments of the present disclosure are directed to proving spaced apart sterilization lights configured to sterilize pathogens on surfaces of a vehicle cabin.

In some embodiments, a pathogen sterilization light assembly for a vehicle cabin includes a plurality of sterilization lights mounted at spaced apart locations along a cabin of the vehicle and configured to emit ultraviolet light directed toward areas within the cabin to sterilize pathogens. The sterilization effects are provided both on illuminated surfaces and the intervening air volume between the sterilization lights and the surfaces.

In some further embodiments, the sterilization lights are divided into groups and the sterilizing light assembly further includes a power controller and power switches which are connected to alternate between allowing power distribution from a power supply and ceasing power distribution from the power supply to different ones of the groups of the sterilization lights. The power controller is configured to separately control the power switches to select which of the groups of the sterilization lights are powered by the power supply at a time. The power controller may select a group of the power switches to power-on to supply power to the sterilization lights which direct UV light toward a prioritized passenger seat or row of passenger seats, based on flight information that includes at least one of: a duration of time between passenger deboarding at the end of a flight and passenger boarding for a next flight; a seating assignment that indicates which passenger seat or rows of passenger seats have been occupied on a previous flight; and a seating assignment that indicates which passenger seat or rows of passenger seats are assigned to be occupied on a next flight.

In some further embodiments, a power controller selects which of the sterilization lights are powered on at a time based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

In a further embodiment, the power controller is configured to control duration of power supplied to which of the sterilization lights based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed. Controlling duration of power supplied can include initiating and ceasing supply of power to selected one(s) of the sterilization lights, and/or can include controlling a level of power supplied to selected one(s) of the sterilization lights to control intensity of the light emitted therefrom (e.g., high output intensity versus low output intensity).

In some further embodiments, a power controller is configured to select a group of the sterilization lights to be powered-on during a sterilization procedure based on flight information that includes at least one of: a duration of time between passenger deboarding at the end of a flight and passenger boarding for a next flight; a seating assignment that indicates which passenger seats or rows of passenger seats were occupied on a previous flight; and a seating assignment that indicates which passenger seats or rows of passenger seats are to be occupied on a next flight, and to further control initiation and cessation of supply of power to the selected group of the sterilization light.

In some further embodiments, a rotational motor is configured to rotate at least one of the sterilization lights relative to at least one passenger seat to scan a focused beam of ultraviolet light along surfaces of the at least one passenger seat. A controller is connected to control the rotational motor to control angular rotation, range of rotation, and/or rate of angular rotation of the at least one sterilization light based on information indicating at least one of: whether the at least one passenger seat has been occupied on a previous flight; whether the at least one passenger seat is assigned to be occupied on a next flight; how many times the at least one passenger seat has been occupied on previous flights since a last sterilization process has been performed; and/or a total time duration the at least one passenger seat has been occupied on one or more previous flights since a last sterilization process has been performed.

Other pathogen sterilization light assemblies, methods of operating, and computer program products for operating according to embodiments of the inventive subject matter will be or become apparent to one with skill in the art upon review of the following drawings and detailed description. It is intended that all such additional pathogen sterilization light assemblies and related methods and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Although various embodiments of the present invention are explained herein in the context of an airplane environment, other embodiments of pathogen sterilization light systems/assemblies and related components are not limited thereto and may be used in other environments, including other vehicles such as ships, submarines, buses, trains, commercial/military transport aircraft, and automobiles, as well as buildings such as conference centers, sports arenas, hotels, homes, etc. Accordingly, in some embodiments users are referred to, in a non-limiting way, as passengers. Passengers may include people who buy tickets, crew members, and/or other representatives of the vehicle operators, including without limitation, employees and representatives of airline, train, automobile, cruise ship, and bus operators. The term passenger can therefore be interchangeably replaced with the term person to refer to anyone who is or was present in a vehicle and/or building configured according to one or more embodiments disclosed herein.

When passengers exit a vehicle, they leave behind pathogens including viruses, bacteria, fungi, protozoa, and worms that the passengers exhaled, transferred by touch, or otherwise transferred to surfaces of the vehicle and air therein. In order to remove or otherwise render harmless those pathogens, Ultraviolet germicidal irradiation (UVGI) may be used to sterilize the surfaces and air within the vehicle.

UVGI can kill or render harmless viruses, bacteria, fungi, protozoa, and worms and other pathogens on a surface that is exposed to emitted UV light, at germicidal wavelengths. Exposing pathogens on a surface or in the air to emitted UV light damages or renders them harmless by, for example, destroying nucleic acids and disrupting the pathogens' DNA.

Figure 1:
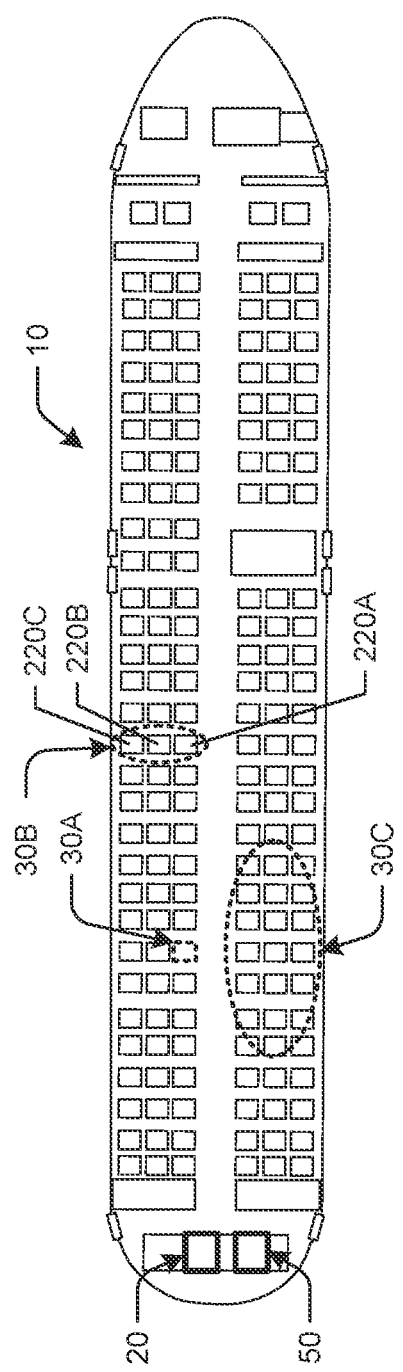
FIG. 1 illustrates a top view of an aircraft cabin with a pathogen sterilization light assembly configured according to some embodiments of the present disclosure.

FIG. 1 illustrates a top view of an aircraft cabin 10 with a pathogen sterilization light assembly configured according to some embodiments of the present disclosure. The aircraft cabin 10 includes rows of passenger seats (e.g., first passenger seat 200A, second passenger seat 200B, and third passenger seat 200C) and a pathogen sterilization light assembly.

The pathogen sterilization light assembly may include a plurality of sterilization lights mounted at spaced apart locations along a cabin of a vehicle. The sterilization lights may be configured to emit ultraviolet (UV) light directed toward areas within the cabin to sterilize pathogens. The area within the cabin may be a surface of an individual passenger seat 30A (herein referred to as a passenger seating surface), a row of passenger seats 30B, and/or a plurality of rows of passenger seats 30C.

The sterilization lights may be at least one of short-wave ultraviolet lamps, incandescent lamps, gas-discharge lamps, ultraviolet light emitting diodes, ultraviolet lasers, and vacuum ultraviolet devices, or other type of UV light emitting device which may be configured to may perform UVGI. The sterilization lights may emit UV-A, UV-B, UV-C light, or Far-UV Sterilray light.

For example, the sterilization lights may produce UV-C light with a wavelength between 100 nm and 280 nm. In another example, the sterilization lights may produce Far-UV Sterilray light. Far-UV Sterilray light has a wavelength of about 207 nm-22 nm and may be less damaging to humans than some UV-C light, which can enable Far-UV Sterilray light to be used in the presence of people within the cabin.

However, it should be understood that the sterilization lights may emit UV light at any wavelength (i.e., germicidal wavelengths) and a sufficient intensity to at least partially sterilize pathogens in an illuminated area of the cabin. Some of the sterilization lights within the cabin may emit ultraviolet wavelengths that are different than some other sterilization lights in the cabin. Any combination of ultraviolet emission intensity and ultraviolet wavelengths which are sufficient to at least partially sterilize pathogens in an illuminated area of the cabin may be used by a sterilization light herein.

The pathogen sterilization light assembly may further include one or more power supplies 20, also referred to as suppl(ies) 20. The power supply 20 may be located anywhere in the vehicle. In some embodiments, the power supply 20 is located in the back of the vehicle and is connected to powerlines that transport the power along the vehicle to the sterilization lights.

The power supply 20 may be the same power supply that supplies power through powerlines to seat located reading lights and/or to seat video display units (SVDUs) located at passenger seats and configured to display video and provide audio out for entertainment content (e.g., movies, television shows, games, electronic books, crew announcements, etc.). The power supply 20 may be connected to a power distribution circuit that is connected to powerlines that distribute the power to the sterilization lights, reading lights, and/or SVDUs. The distributed power may be voltage down-converted and/or converted from alternating to direct current by local converters intervening between the powerlines and the one or group of the sterilization lights, reading lights (e.g., overhead reading lights for seats), and/or SVDUs, e.g., positioned relative to seats along a row. Alternatively, the power supply 20 may be connected to a power distribution circuit that is connected to powerlines that are separate than those of the powerlines that distribute power to the reading lights and/or SVDUs.

The power supply 20 and the distribution of power will be discussed further with regards to FIG. 5 below.

The pathogen sterilization light assembly may further include a power controller 50 that controls the power supply 20 to provide power to sterilization lights (or groups of sterilization lights). In one embodiment the power controller 50 initiates supply of power to an individual sterilization lights and/or to groups of sterilization lights responsive to signaling from at least one proximity sensor indicating no persons are in the area. In a further embodiment, the power controller 50 interrupts the supply of power to the individual sterilization lights and/or to groups of sterilization lights responsive to signaling from the at least one proximity sensor indicating a person has become present in the area. The power controller 50 may be powered by the power supply 20 or by another power source.

The proximity sensor may be a camera, passive infrared sensor, weight sensor, thermal sensor, Bluetooth sensor, or other type of sensor that is configured to detect the presence of a person or a device on a person within a monitored area, such as a row of seats or a section of the aircraft cabin. In some embodiments, a plurality of proximity sensors is spaced apart along the aircraft cabin to monitor spaced apart areas for presence of a person, such as at each entrance of the aircraft, or a single proximity sensor may be located within the vehicle. The proximity sensor(s) can detect the presence of a person by detecting motion by a person, shape of a person, or presence of an electronic device transportable by a person (such as by detecting RF signaling of: a mobile phone, laptop computer, tablet, etc.) that can indicate presence of a person. The electronic device may be detected through Bluetooth signaling, WiFi signaling, and/or NFC signaling transmitted by the electronic device and received (sensed) by the proximity sensor.

Since some wavelengths and intensities of UV light can be damaging to human skin and cell DNA, in some embodiments the sterilization lights are only activated when the corresponding illuminated areas, such as passenger seating surfaces, are no occupied by a passenger or when the vehicle is empty of persons. If a sensor indicates to the power controller 50 that a person is detected in an area, e.g., within or sufficiently near the area to be sensed, then the power controller 50 can deactivate or not activate the corresponding sterilization light or group of sterilization lights that is arranged and configured to emit UV light toward that area. Thus, for example, the power controller 50 can be configured to sterilize one section or seat row of the aircraft cabin while one or more crew or other passengers are present in another section or sufficiently spaced apart other seat row of the aircraft cabin.

The power controller 50 is discussed further with reference to FIG. 5 below.

Figure 2A:
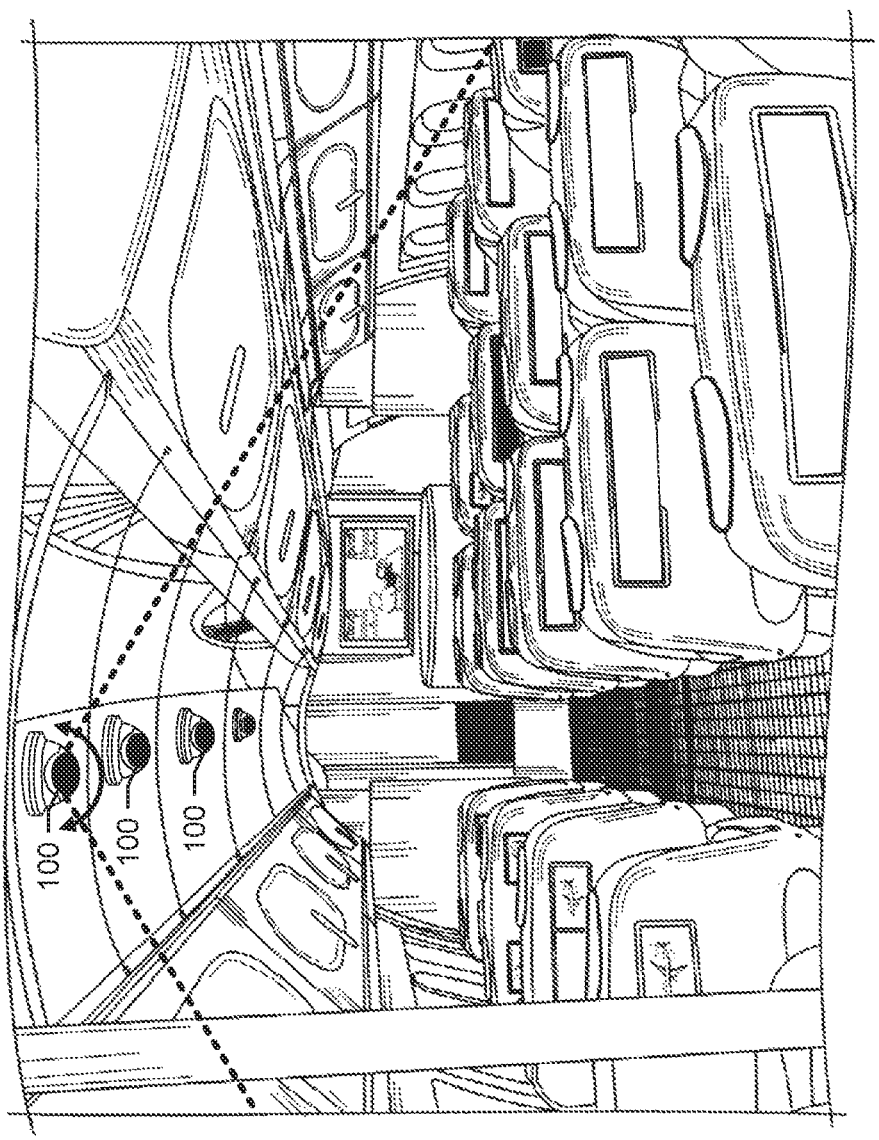
FIG. 2A-C illustrates a view of an aircraft cabin with sterilization lights configured according to some embodiments of the present disclosure.

FIG. 2A illustrates an aircraft cabin with sterilization lights 100 configured to be at least partially integrated within a ceiling structure above an isle within the cabin. The sterilization lights receive power from a power source via powerlines extending along the ceiling. The sterilization lights 100 may be mounted, and have a beam angle, to direct UV light toward at least one of: the isle, a passenger seat, and a row of passenger seats. For example, the sterilization lights 100 may have a narrow beam angle that only directs UV light toward the isle, or toward a single passenger seat. In another example, the sterilization lights 100 may have a beam angle that is sufficiently wide to direct UV light toward a row of passenger seats and/or an isle and row of passenger seats.

In some embodiments, a narrower beam angle may be preferred because in order for the UV light to sterilize a surface, the UV light has to produce a sufficient dosage of UV light to the area during a threshold time interval to at least partially sterilize pathogens on illuminated surfaces within the area. The sufficient dosage can be defined by an intensity and duration to cause sterilization of at least one or more defined types of pathogens which the pathogen sterilization light assembly targets to sterilize (e.g., one or more defined types of viruses, such as Covid-19 and/or other type of coronavirus, and/or one or more types of bacteria, such as *Streptococcus pyogenes*). Dosage can be the intensity of the UV light multiplied by the duration for which the UV light is directed toward the area. So, the greater the intensity or the greater the duration, the greater the dosage. Intensity is inversely proportional to the square of a distance between the UV light source and the area to be sterilized. Therefore, the further away the sterilization light is from the surfaces in the area to be sterilized, the lower the dosage will be for a specific duration of time when compared to smaller distances over the same duration. Additionally, intensity is affected by the beam angle, such that a wider beam angle may produce a lower dosage over a specified duration of time when compared to a narrower (more focused) beam angle over the same duration.

The duration for which the sterilization lights is be required to direct light towards the area to attempt to achieve a defined level of sterilization can depend on the intensity of the sterilization lights. If the sterilization lights produce a lower intensity, then the necessary duration to produce the sufficient dosage will be longer. If the sterilization lights produce a higher intensity, then the necessary duration to produce the sufficient dosage will be shorter. In some embodiments, groups of sterilization lights are sequentially powered-on and then powered-off one at a time to enable higher power level to be provided to the sequentially powered groups of sterilization lights to support higher intensity emissions from the sterilization lights while powered and avoid need for a higher rated power suppl(ies) 20 and/or power distribution wiring between the power suppl(ies) 20 and the groups of sterilization lights.

In some other embodiments, the intensity of light emitted by groups of sterilization lights is sequentially switched between different intensities (e.g., higher dosage faster sterilization level and lower dosage slower sterilization level) one at a time to enable higher dosages to be output by the sequentially powered groups of sterilization lights to support sterilization of corresponding sequentially selected areas within the cabin while avoiding need for a higher rated power suppl(ies) 20 and/or power distribution wiring between the power suppl(ies) 20 and the groups of sterilization lights. Controlling the groups of lights to provide different intensities may enable use of a shorter duration higher-intensity which may be more effective against certain types of pathogens and a longer duration lower-intensity which may be more effective against some other types of pathogens.

In some embodiments, one or more of the sterilization lights 100 can be connected to rotational motors configured to rotate the sterilization light to scan a more narrowly focused beam of UV light along passenger seating surfaces of at least one passenger seat. The term "motor" is used to generally refer without limitation to any type of motor or linear/servo actuator assembly that is configured to angularly rotate one or more sterilization lights between at least two angular orientations, and which may have a range of angular rotation and/or a range of rotational velocity that is controllable by a controller. For example, between flights a controller may set a smaller range of angular rotation and a faster velocity to scan one or more times a focused beam of UV light across a particular area (e.g., arm rests) or defined set of subareas (e.g., arm rest, seat tray, and headrest) to perform a quick sterilization of pathogens on certain surfaces between flights.

The controller may control the motor to incrementally step the focused beam of UV light to scan in each of a plurality of spaced apart defined areas that are designated as a high priority for sterilization, and skipping over scanning of intervening areas that are relatively lower priority for sterilization. For example, the controller may define a plurality of spaced apart ranges of annular rotation (e.g., first angular range, a non-overlapping second angular range, non-overlapping third angular range, etc.) and control how long a sterilization light scans within each of the spaced apart ranges of angular rotation. The controller may operate to provide longer duration sterilization light scans in one of the ranges of angular rotation relative to one or more other ranges of angular rotation. In a further example, the controller may control the motor to scan the focused beam of UV light constrained to a first rotational range of motion (e.g., to direct the focused beam of UV light to scan one or more times across only a limited area that corresponds to the seat headrest) for a first time duration, then control the motor to incrementally rotate the sterilization light to scan the focused beam of UV light constrained to a second rotational range of motion (e.g., to direct the focused beam of UV light to scan across one or more times only a limited area that corresponds to the seat arm rests) for a second time duration, etc. Controlling the size of the scanned areas and the duration of the scanning enables the controller to control how long the sterilization process takes to complete, which can be beneficial for use for relatively short flight layovers while the aircraft is not-occupied by passengers between flights. Moreover, controlling the size of the scanned areas and the duration of the scanning enables the controller to control the level of effectiveness of the sterilization against targeted types of pathogens. For example, headrest areas may be provided the highest effective treatment while lower seat areas may be provided a lower effective treatment, e.g., during brief layovers between flights.

Although various embodiments are described in the context of scanning the beam of UV light across the areas, in some other embodiments the beam of UV light is directed to one of the defined areas at a time and then remains rotationally fixed for a defined time duration to expose the entire directed area without scanning a narrower beam across the area (i.e., the UV light beam has an angular width sufficient to expose the targeted surface in defined area). In the example above, the motor may direct the UV light beam at a first area (e.g., seat headrest surfaces) for a first time duration, then step the motor to direct the UV light beam at a second area (e.g., seat arm rest surfaces) for a second time duration, etc.

During a longer layover between flights (e.g., parked overnight) the controller may increase the range of angular rotation and scan duration to scan one or more times a focused beam of UV light across a much wider area (e.g., angularly from the floor, across the seat, armrests and seat tray, to the ceiling) to thoroughly sterilize pathogens present on surfaces throughout the wide range of motion of the sterilization lights.

The passenger seating surfaces may be any surface on a passenger seat and may include, but are not limited to, at least one of: a seat back surface (e.g., the back exposed surface of the passenger seat); a headrest surface (e.g., the surface that supports the head of a passenger when seated in the passenger seat); an armrest surface; and a seat cushion surface. For example, the sterilization lights 100 may repetitively rotate from left to right and vice-versa to scan across a row of passenger seats, an aisle, and an opposite adjacent row of passenger seats.

In some embodiments, the controller obtains an indication of how long the aircraft will remain unoccupied between flights e.g., accesses a flight schedule for a particular aircraft, and responsively determines the duration of the sterilization process that will be performed based on the indication. For example, the controller may be configured to respond to an indication of a 30 minute layover by defining a fewer number of areas of a seating surface to be sterilized and responsively control the motor to dwell the UV light beam on just those defined areas for a majority of or all of the layover time to prioritize sterilization thereof during the available time, such as by rotationally stepping the sterilization light to different angular orientations each for a fractional part of the layover time duration and/or scan the sterilization light within different angular ranges each for a fractional part of the layover time duration. In contrast, the controller may be configured to respond to an indication of a 2 hour layover by defining a greater number of areas of a seating surface to be sterilized and responsively control the motor to dwell the UV light beam on just the greater number of defined areas for the 2 hour layover time to prioritize sterilization thereof during the available time.

Herein, rotational motors may include any electrical machine that can convert electric energy into rotational movement of attachment structure in order to rotate the sterilization light. The rotation of the sterilization lights may be configured to have a rotational velocity to produce a sufficient UV exposure dosage to achieve desired sterilization on the area or passenger seating surfaces. The rotation may be a slow continuous rotation or a rotation that stops at incremental rotational angles along the arc in order to provide a duration long enough to produce a sufficient UV exposure dosage to different passenger seating surfaces.

Thus, in one embodiment, the pathogen sterilization light assembly further includes a power controller configured to select a group of the sterilization lights to be powered-on during a sterilization procedure based on flight information that includes at least one of: a duration of time between passenger deboarding at the end of a flight and passenger boarding for a next flight; a seating assignment that indicates which passenger seats or rows of passenger seats were occupied on a previous flight; and a seating assignment that indicates which passenger seats or rows of passenger seats are to be occupied on a next flight, and to control initiation and cessation of supply of power to the selected group of the sterilization light.

In another embodiment, the pathogen sterilization light assembly further includes a power controller configured to select a group of the sterilization lights to be switched from a lower intensity output to a higher intensity output, or vice versa. The selection of which group(s) of sterilization lights, the rate of switching between groups, and/or the higher intensity level which the group of sterilization lights is controlled to switch to during a sterilization procedure can be based on flight information that includes at least one of: a duration of time between passenger deboarding at the end of a flight and passenger boarding for a next flight; a seating assignment that indicates which passenger seats or rows of passenger seats were occupied on a previous flight; and a seating assignment that indicates which passenger seats or rows of passenger seats are to be occupied on a next flight.

In another embodiment, the pathogen sterilization light assembly assembly further includes a rotational motor and a controller. The rotational motor is configured to rotate at least one of the sterilization lights relative to at least one passenger seat to scan a focused beam of ultraviolet light along surfaces of the at least one passenger seat. The controller is connected to control the rotational motor to control angular rotation, range of rotation, and/or rate of angular rotation of the at least one sterilization light based on information indicating at least one of: whether the at least one passenger seat has been occupied on a previous flight; whether the at least one passenger seat is assigned to be occupied on a next flight; how many times the at least one passenger seat has been occupied on previous flights since a last sterilization process has been performed; and/or a total time duration the at least one passenger seat has been occupied on one or more previous flights since a last sterilization process has been performed.

In another embodiment, the pathogen sterilization light assembly assembly further includes a rotational motor and a controller. The rotational motor is configured to rotate at least one of the sterilization lights relative to at least one passenger seat to direct a focused beam of ultraviolet light toward surfaces of the at least one passenger seat. The controller is configured to define a set of areas of a seating surface to be sterilized, and to control the rotational motor to incrementally step a focused beam of UV light of one of the at least one of the sterilization lights from being directed toward a first area in the set in which a sterilization process has been performed to become directed at a second area in the set to initiate the sterilization process the second area while rapidly skipping over an intervening area between the first and second areas without performing the sterilization process in the intervening area.

In another embodiment, the pathogen sterilization light assembly assembly further includes a controller that is configured to define a number of areas in the set to incrementally step the the at least one of the sterilization lights between to perform the sterilization process on based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

In another embodiment, the pathogen sterilization light assembly assembly further includes a controller that is configured to control which of the sterilization lights is powered by a power supply at a time, and to select which of the sterilization lights are powered on at a time based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

In a further embodiment, the power controller is further configured to control which of the sterilization lights is powered by a power supply at a time, and to control duration of power supplied to which of the sterilization lights based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

Figure 2B:
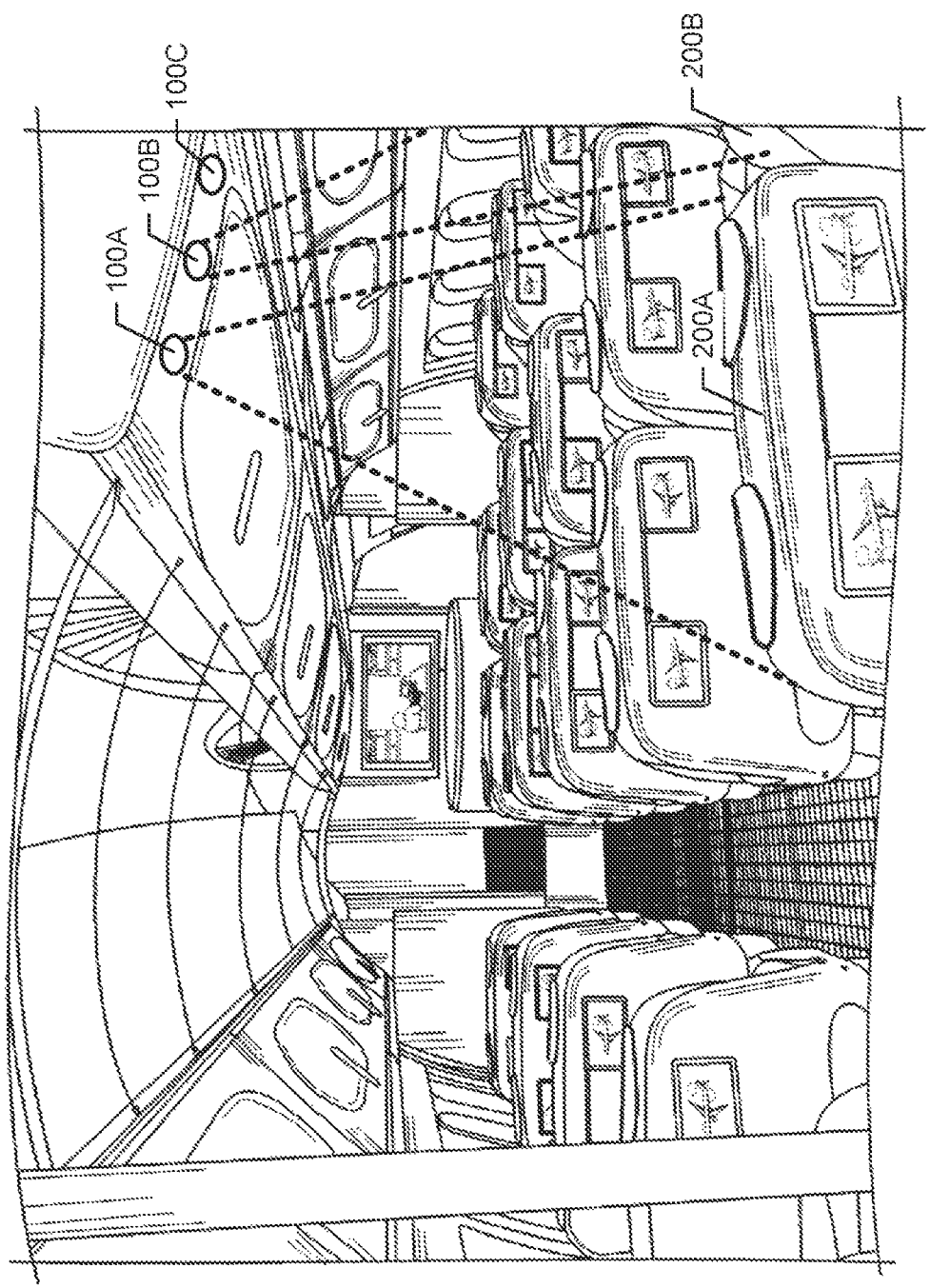

FIG. 2B illustrates an aircraft cabin with sterilization lights 100A-C configured to be at least partially integrated within a ceiling structure above passenger seats within the cabin. The sterilization lights 100A-C may be powered by powerlines extending along the ceiling. The sterilization lights 100A-C may be configured to operate in dual modes: a reading mode emitting safe visible wavelength light for passenger reading or comfort while seated; and a sterilization mode emitting predominantly UV wavelength light for sterilizing pathogens. Each of the lights may include a pair of emitters (e.g., a light fixture with two differently configured emitter circuits), with one of the emitters configured to emit safe visible wavelength light and the other emitter configured to emit predominantly UV wavelength light, and a switch circuit that selectively activates one of the two emitters of the pair based on a control signal from the controller, where the switching may be responsive to a mode selection. The mode selection may be controlled based on a proximity sensor, such as to prevent operation of the sterilization mode while the proximity sensor detects presence of a person.

In some embodiments, the sterilization lights 100A-C are each mounted to direct UV light toward at least one of: a passenger seat, a row of passenger seats, and an isle and a plurality of passenger seats within the vehicle. For example, in FIG. 2B, sterilization light 100A is mounted to direct UV light toward a passenger seat 200A, sterilization light 100B is mounted to direct UV light toward an adjacent passenger seat 200B, and sterilization light 100C is mounted to direct UV light toward another adjacent passenger seat.

In some embodiments, each of the sterilization lights (e.g., sterilization lights 100A-C) are connected to a rotational motor configured to rotate the sterilization lights (e.g., sterilization lights 100A, 100B, and/or 100C) to scan respective focused beams of UV light along passenger seating surfaces (e.g., seat back surfaces, armrest surfaces, seat cushion surfaces, headrest surfaces, etc.).

For example, in FIG. 2B, there may only be the sterilization light 100B above the passenger seat 200B within the cabin. Sterilization light 100B may be connected to a rotational motor configured to angularly rotate the sterilization light 100B to scan a focused beam of UV light along the passenger seating surfaces of passenger seat 200B, passenger seat 200A, and any other adjacent seat. In another example, of FIG. 2B, there may be both sterilization light 100A and sterilization light 100B that may be connected to a rotational motor configured to rotate the sterilization lights 100A-C to scan respective focused beams of UV light along the same (or different) passenger seating surfaces of passenger seat(s) 200A, 200B, and/or another adjacent seat. By having more than one sterilization light scanning a focused beam of UV light along the same passenger seating surface of the same passenger seat, the more than one dosages emitted by the more than one sterilization light to the passenger seating surface allows for the dosages from each sterilization light to be added together. This may decrease the time duration needed to produce a sufficient dosage to sterilize at least some of the pathogens on the passenger seating surfaces.

Figure 2C:
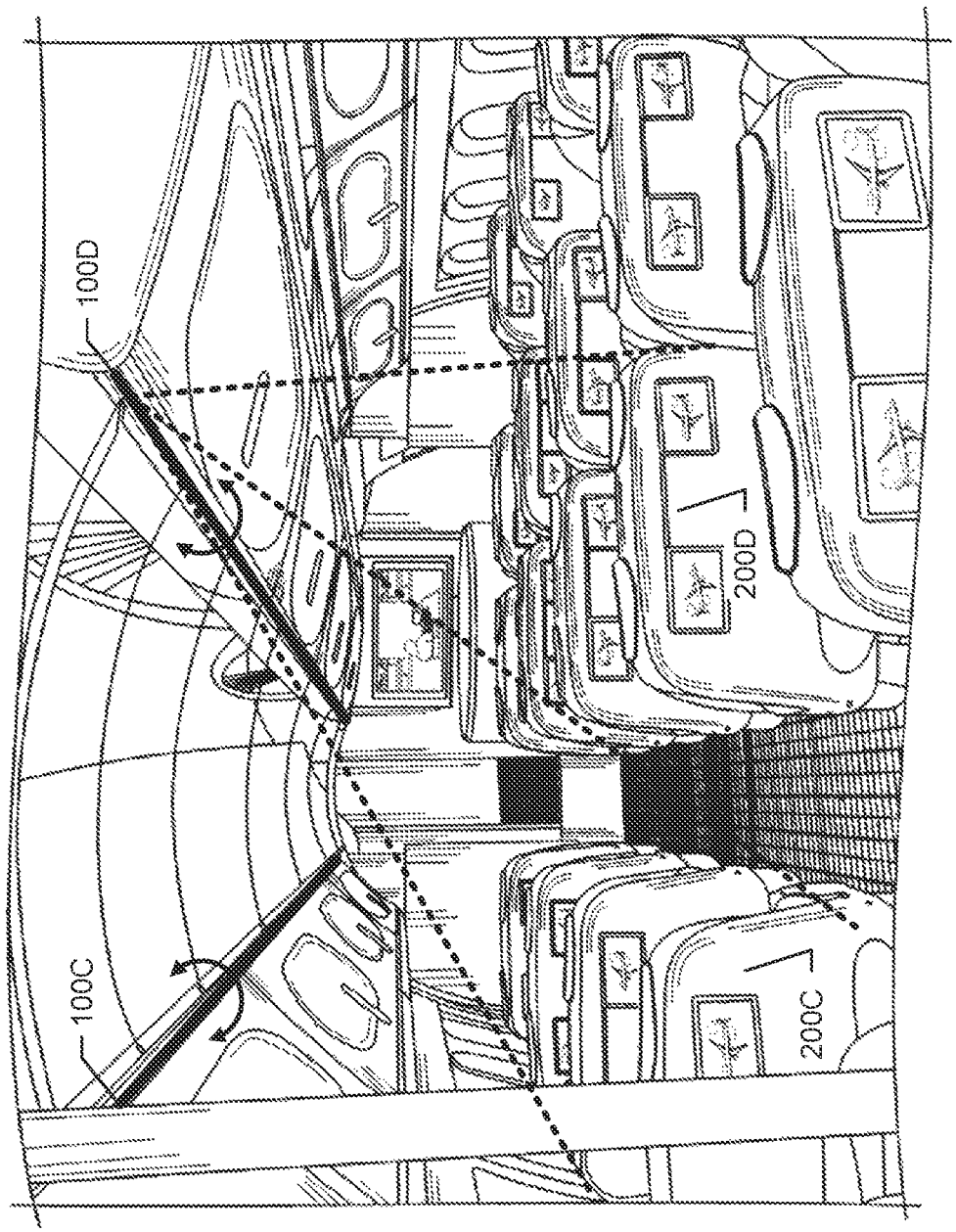

FIG. 2C illustrates an aircraft cabin with sterilization lights 100C and 100D configured to be at least partially integrated within an overhead storage compartment structure and/or a ceiling structure above passenger seats within the cabin. The sterilization lights 100C-D may each be a single UV light source longitudinally extending along one or more rows of seats or may be a plurality of UV light sources spaced apart along one or more rows of seats. The sterilization lights 100C-D may be powered by powerlines extending along the ceiling.

In some embodiments, the sterilization lights 100C-D are each mounted to direct UV light toward at least one of: a passenger seat, a row of passenger seats, and an aisle and a plurality of passenger seats within the vehicle.

In some embodiments, each of the sterilization lights 100C-D are connected to a rotational motor configured to angularly rotate the sterilization light to scan a focused beam of UV light along the aisle and/or passenger seating surfaces of at least one passenger seat adjacent to the aisle.

For example, sterilization light 100D may rotate one or more times between a downward direction to scan a UV beam across a passenger seat 200D and an upward direction to scan the UV across another passenger seat 200C, or vice versa. As the sterilization light 100D rotates upward, the sterilization light 100D may scan the UV beam across the aisle between the passenger seats 200D and 200C.

Figure 3:
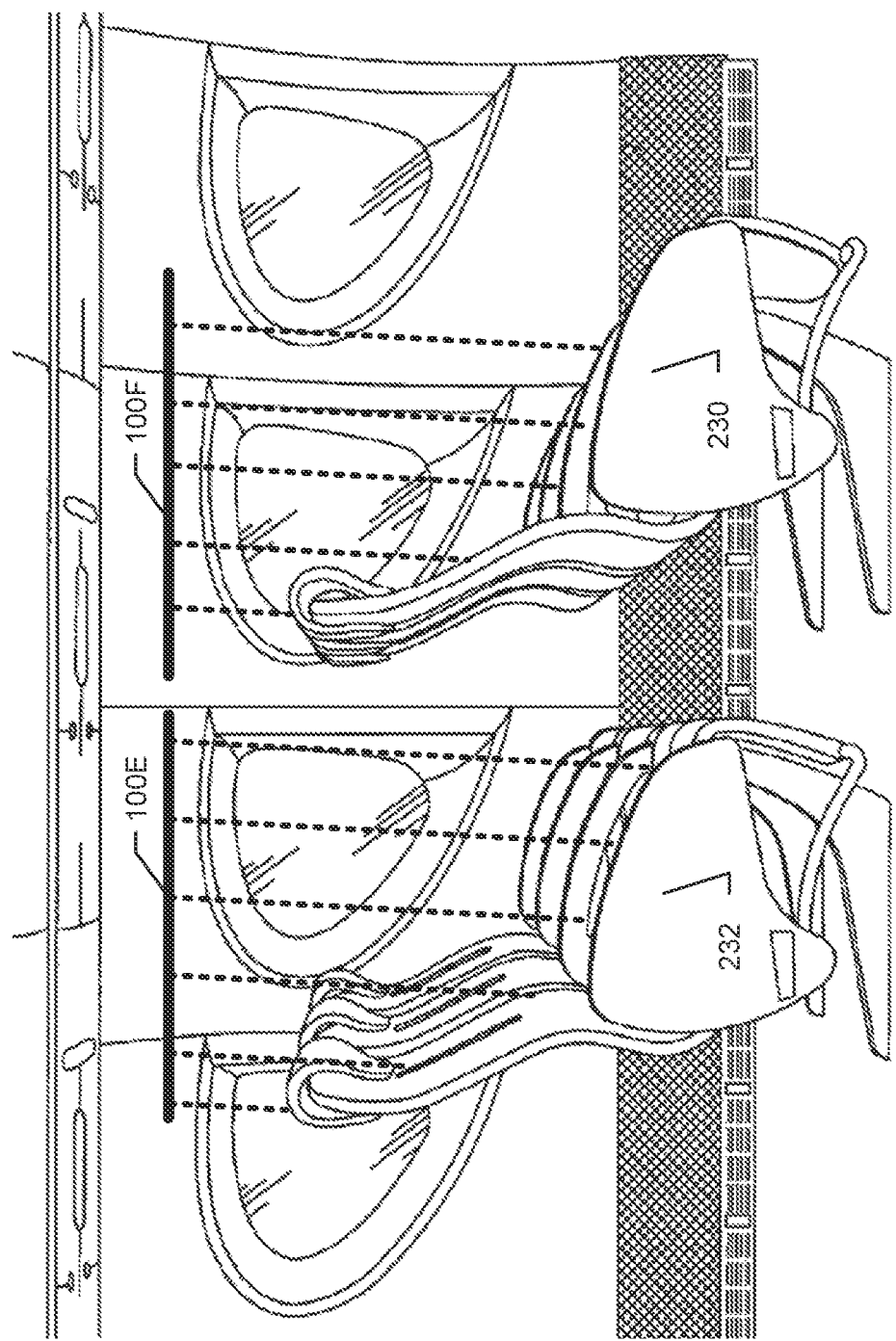
FIG. 3 illustrates a side view of two rows of passenger seats within a vehicle cabin with sterilization lights configured according to some embodiments of the present disclosure.

FIG. 3 illustrates a side view within an aircraft cabin of two rows 230/232 of passenger seats and sterilization lights 100E-F configured to be at least partially integrated within a wall structure of the cabin to direct UV light toward a row of passenger seats. The sterilization lights 100E-F may each be one elongated sterilization light horizontally mounted, a plurality of sterilization lights that are spaced apart horizontally relative to each other, or a plurality of sterilization lights that are spaced apart vertically relative to each other. The sterilization lights 100E-F may be powered by powerlines extending along the wall structure.

In some embodiments, sterilization light 100E may be one or more sterilization lights that direct a focused UV beam towards one or more passenger seats within the row 232 of passenger seats. For example, there may be a sterilization light for each passenger seat in the row 232 that directs UV light toward a different one of the passenger seats in the row 232. Alternatively, there may be one sterilization light that directs a wide beam angle of UV light towards all of the passenger seats in the row 232.

In some embodiments, there are one or more sterilization lights that are connected to rotational motors that angularly rotate the sterilization light(s) to scan a focused beam of UV light along passenger seating surfaces of one or more of the passenger seats in the row 232.

Figure 4A:
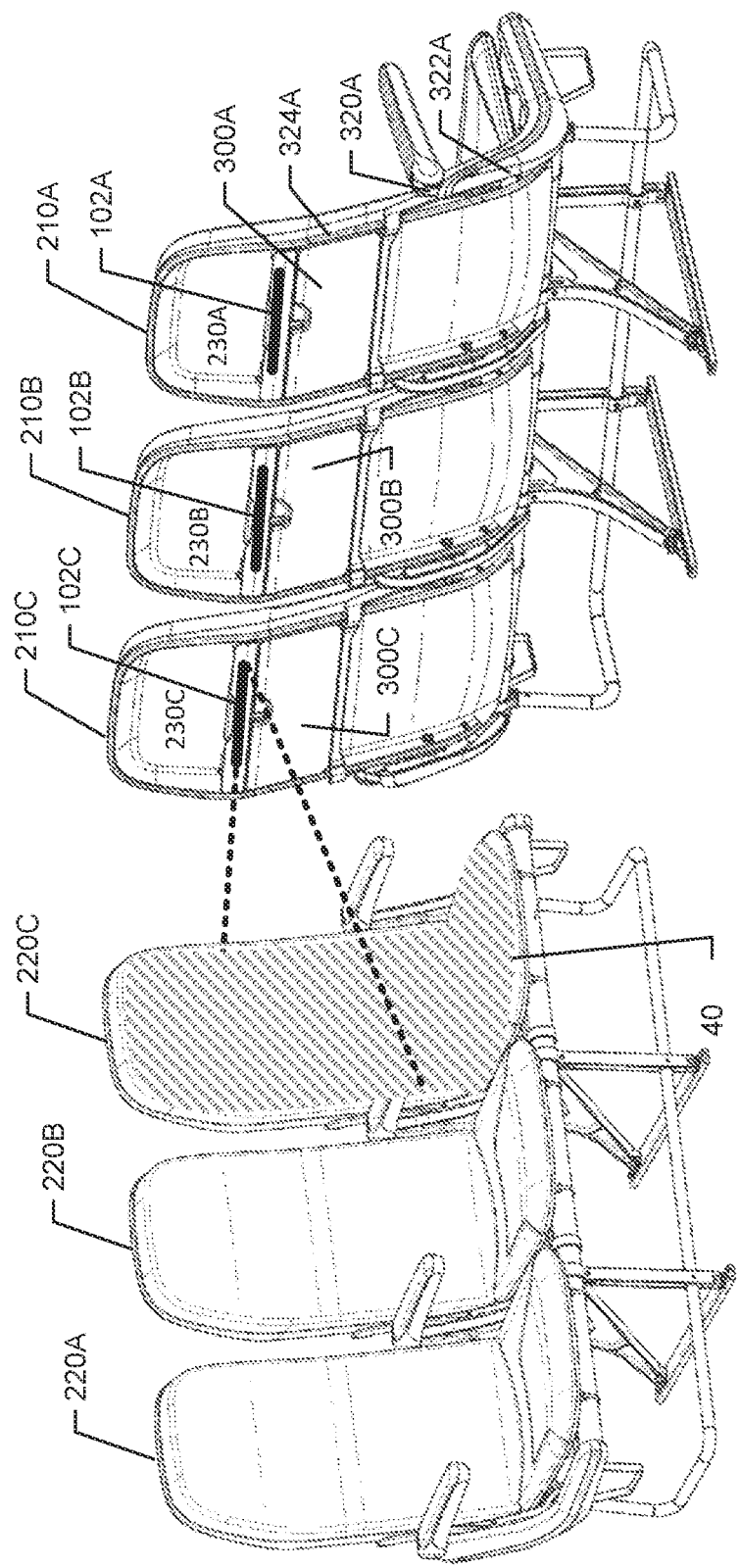
FIG. 4A-B illustrates a row of passenger seats with sterilization lights partially integrated within a back surface of the passenger seats and which are configured according to some embodiments of the present disclosure.

FIG. 4A illustrates a row of passenger seats with sterilization lights 102A-C at least partially integrated within a back surface of the passenger seats 210A-C respectively. The sterilization lights 102A-C may be mounted below SVDUs 230A-C and above deployable seat trays in the seatbacks. The sterilization lights 102A-C may be powered by powerlines extending within the passenger seats. The sterilization lights 102A-C may be supplied power from a power source that powers SVDUs 230A-C in the seatbacks. In some other embodiments, the sterilization lights 102A-C are at least partially embedded within respective housings of the SVDUs 230A-C and may be powered by one or more power sources that also power of the SVDUs 230A-C.

In some embodiments, the sterilization lights 102A-C emit UV light toward at least one of passenger seating surfaces of passenger seats 220A-C located behind and facing the passenger seats 210A-C and trays 300A-C which deploy from the back surface of the passenger seats 210A-C respectively. In FIG. 4A, the passenger seats 220A-C have been illustrated as being offset 90 degrees from the passenger seats 210A-C to facilitate illustration of the sterilization lights, trays, SVDUs, etc.

For example, the sterilization light 102C may direct UV light toward a passenger seating surface 40 of the other passenger seat 220C located behind the passenger seat 210C. The sterilization light 102C may additionally direct UV light toward a tray 300C of the passenger seat 210C.

Whether the sterilization lights 102A-C direct UV light toward the trays 300A-C may depend on the position of the trays 300A-C. For example, while the tray 300C is deployed in a down position the sterilization light 102C may direct UV light toward the deployed horizontal surface of the tray 300C. In contrast, while the tray 300C is stored in an upright position (as depicted in FIG. 4A) the horizontal surface of the tray 300C is concealed from the UV light emitted by the sterilization light 102C.

While only one sterilization light has been illustrated as being at least partially integrated in the back surface of each passenger seat, more than one sterilization light may be integrated in each passenger seat and configured to direct UV light toward each of the passenger seating surfaces of each of the passenger seat, including, but not limited to, a headrest surface, a seat back surface, an armrest surface, and a seat cushion surface. The sterilization light(s) may be mounted in the back surface 320A of the armrest, seat support structure 322A, headrest, and/or periphery surface(s) (e.g., 324A) of a forward row seat and with the light(s) arranged to direct UV light toward various passenger seating surface(s) of the passenger seat in a rearward row which faces the forward row seat.

In some embodiments, when there is more than one sterilization light mounted in a passenger seat, the sterilization lights are spaced apart horizontally and/or vertically and angled to focus UV light toward different areas of the passenger seat surfaces. In some embodiments, the sterilization lights are spaced apart vertically and angled to focus UV light toward different vertically spaced apart areas of the passenger seat surfaces.

A potential benefit of having sterilization lights spaced apart vertically is that each of the sterilization lights may be closer to the respective areas of the passenger seating surface which is to be sterilized. By having the sterilization lights closer to the respective areas of the passenger seating surfaces, the dosage of the sterilization lights is greater due to decreased distance between the sterilization light and the passenger seating surface being.

For example, a sterilization light may be located on a back surface of a headrest of the passenger seat and configured to direct light toward a passenger seating surface of a headrest of an adjacent passenger seat located behind the passenger seat. In another example, a sterilization light may be located on a back surface of a lower portion of the passenger seat and configured to direct light toward a passenger seating surface of a seat cushion of another passenger seat located behind the passenger seat.

Figure 4B:
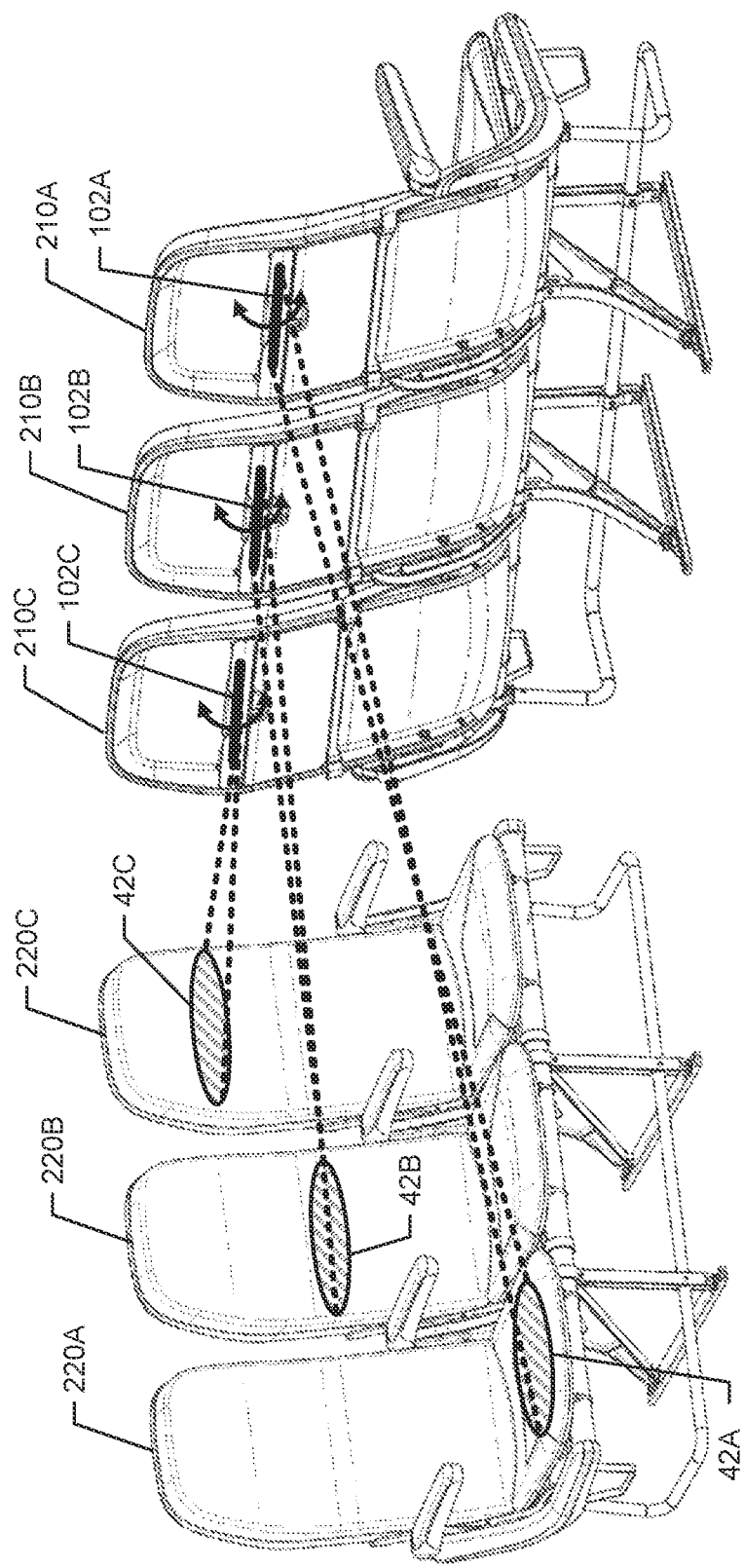

FIG. 4B illustrates a row of passenger seats with sterilization lights 102A-C at least partially integrated within a back surface of the passenger seats 210A-C respectively. The sterilization lights 102A-C may be the same or similar to the sterilization lights of FIG. 4A.

In some embodiments, sterilization lights 102A-C are connected to rotational motors configured to angularly rotate the sterilization lights 102A-C relative to the passenger seats 210A-C to scan a focused beam of UV light along passenger seating surfaces of other passenger seats 220A-C located behind the passenger seats 210A-C.

For example, in FIG. 4B, sterilization light 102A may start at a passenger seating surface 42A located on the seat cushion of passenger seat 220A. The sterilization light 102A may rotate upward to then direct light to a passenger seating surface on the seat back of the passenger seat 220A, and then rotate more to direct light to a passenger seating surface on the headrest of the passenger seat 220A.

In some embodiments, each of the sterilization lights 102B-C on the back surfaces of the passenger seats 210B-C may operate the same as that of sterilization light 102A, such that sterilization lights 102B-C may direct UV light to the same passenger seating surface areas. For example, when sterilization light 102A is directing light to the passenger seating surface 42A on the seat cushion of passenger seat 220A, sterilization light 102B-C may direct UV light toward passenger seating surfaces of the seat cushion areas on passenger seats 220B-C respectively. Therefore, in FIG. 4B, sterilization light 102A may be depicted at a time T1 at a direction angle of the sterilization lights when the sterilization process starts, the direction angle of the sterilization light 102B may be a depiction of the sterilization lights at a time T2 (after T1), and the direction angle of the sterilization light 102C may be a depiction of the sterilization lights at a time T3 (after T2).

In another embodiment, the sterilization lights 102A-C do not rotate at the same time and do not direct UV light toward the same passenger seating surface on each respective passenger seat, but rather direct UV light at different areas of passenger seating surfaces. For example, in FIG. 4B, the sterilization lights 102A-C are depicted at the time T1. Sterilization light 102A may be directing UV light toward a passenger seating surface 42A on the seat cushion of the passenger seat 220A, sterilization light 102B may be directing UV light toward a passenger seating surface 42B on the seat back of the passenger seat 220B, and sterilization light 102C may be directing UV light towards a passenger seat surface 42C on the headrest of the passenger seat 220C.

In another embodiment, a controller is controlled to separately control activation and/or duration of UV light exposure from individual ones of the sterilization lights 102A-C. In a further embodiment the controller is connected to control a rotational motor configured to rotate at least one of the sterilization lights relative to at least one passenger seat to scan a focused beam of ultraviolet light along surfaces of the at least one passenger seat. The controller can be configured to control angular rotation, range(s) of rotation, and/or rate of angular rotation of the at least one sterilization light (e.g., lights 102A-C) based on information indicating at least one of: whether the at least one passenger seat has been occupied on a previous flight; whether the at least one passenger seat is assigned to be occupied on a next flight; how many times the at least one passenger seat has been occupied on previous flights since a last sterilization process has been performed; and/or a total time duration the at least one passenger seat has been occupied on one or more previous flights since a last sterilization process has been performed. For example, the controller may determine from the information whether a sterilization process is to be performed and/or a level of sterilization process which relates to how much total UV light exposure is to be directed to that particular seat and/or how many areas of the seat are to be exposed to UV light and for how long.

Figure 4C:
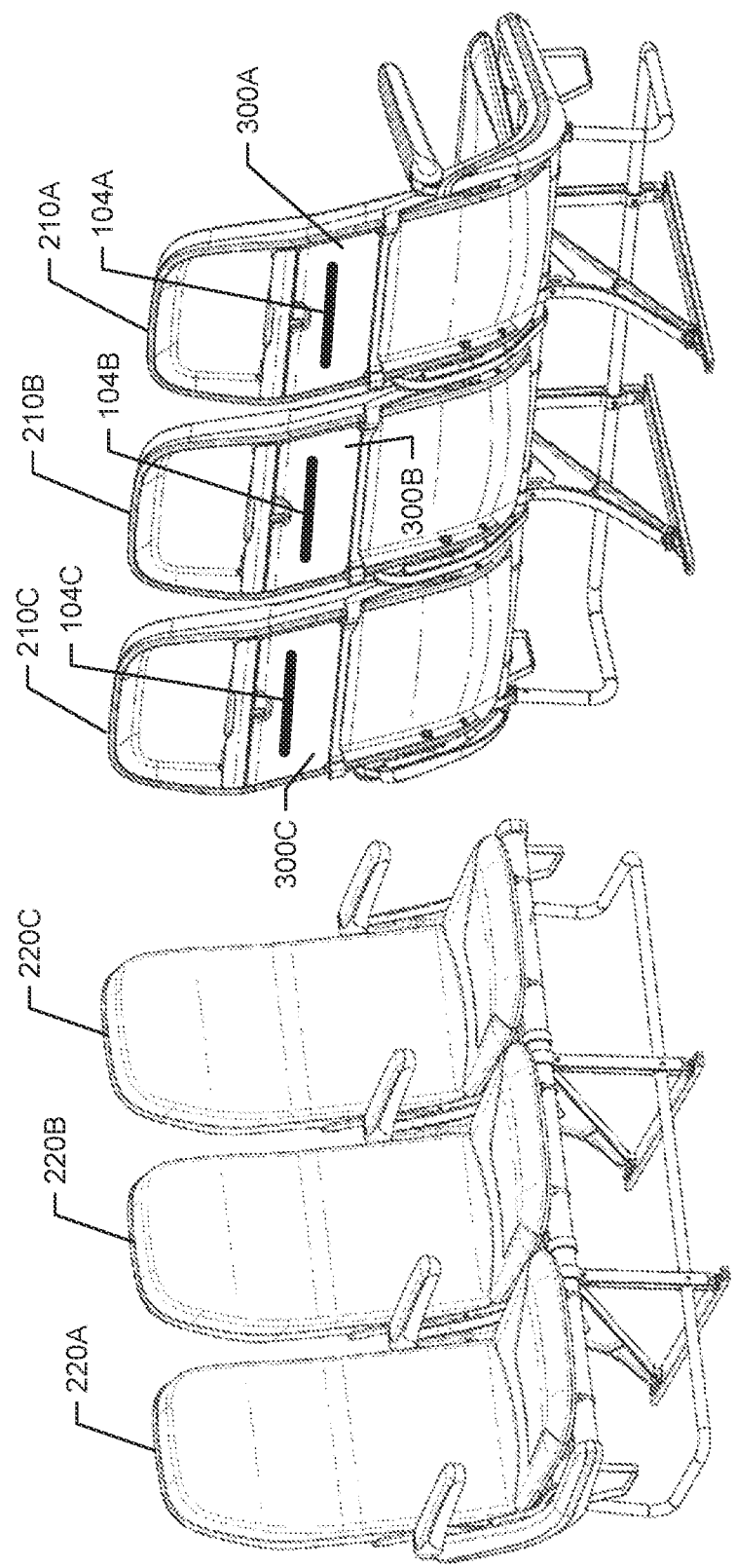
FIG. 4C illustrates sterilization lights each partially integrated within a bottom surface of a tray of passenger seats configured according to some embodiments of the present disclosure.

FIG. 4C illustrates a row of passenger seats with sterilization lights 104A-C at least partially integrated within a tray of the passenger seats 210A-C respectively.

In some embodiments, each of the sterilization lights are partially integrated within at least one of: a bottom surface of a tray extendable from a passenger seat to direct UV light toward a passenger seating surface of another passenger seat located behind the passenger seat while the tray is stored in an upright position; and an end surface of the tray to direct UV light toward the passenger seating surface of the other passenger seat located behind the passenger seat while the tray is deployed in a down position. Additionally, the sterilization lights are powered by powerlines extending through the passenger seats and the trays.

For example, in FIG. 4C, the sterilization lights 104A-C are partially integrated within a bottom surface of trays 300A-C extendable from passenger seats 210A-C respectively, to direct UV light toward a passenger seating surface of other passenger seats 220A-C located behind the passenger seats 210A-C while the trays 300A-C are stored in an upright position.

Figure 4D:
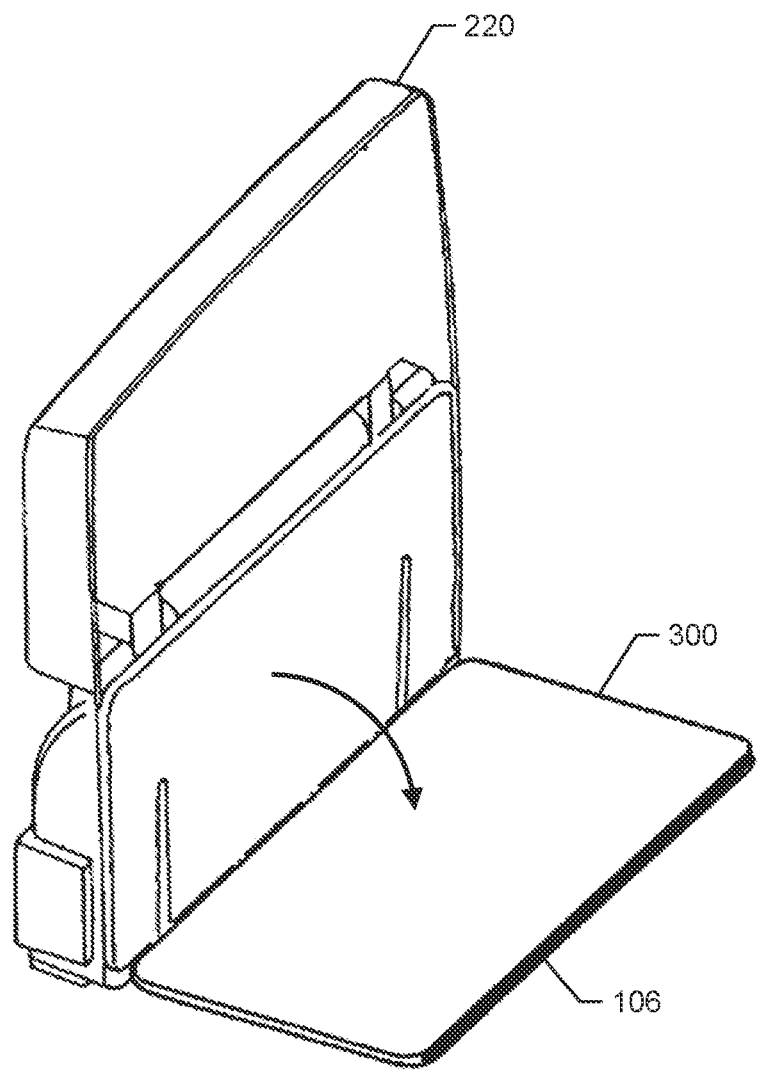
FIG. 4D illustrates a sterilization light partially integrated within an end surface of a tray configured according to some embodiments of the present disclosure.

FIG. 4D illustrates the back of a passenger seat 220 with a sterilization light 106 partially integrated within an end surface of the tray to direct UV light toward the passenger seating surface of the other passenger seat located behind the passenger seat 220 while the tray is deployed in a down position. The sterilization light 106 is powered by powerlines extending through the passenger seats and the trays.

In some embodiments, the sterilization lights 104A-C and 106 are connected to rotational motors and rotate similar to sterilization lights 102A-C above with reference to FIG. 4B.

It is to be understood that any combination of sterilization lights may be used herein. For example, some sterilization lights may be partially integrated within the ceiling at different locations within the cabin, some sterilization lights may be partially integrated in a back surface of a passenger seat, and/or some sterilization lights may be partially integrated in a tray of a passenger seat.

Figure 5:
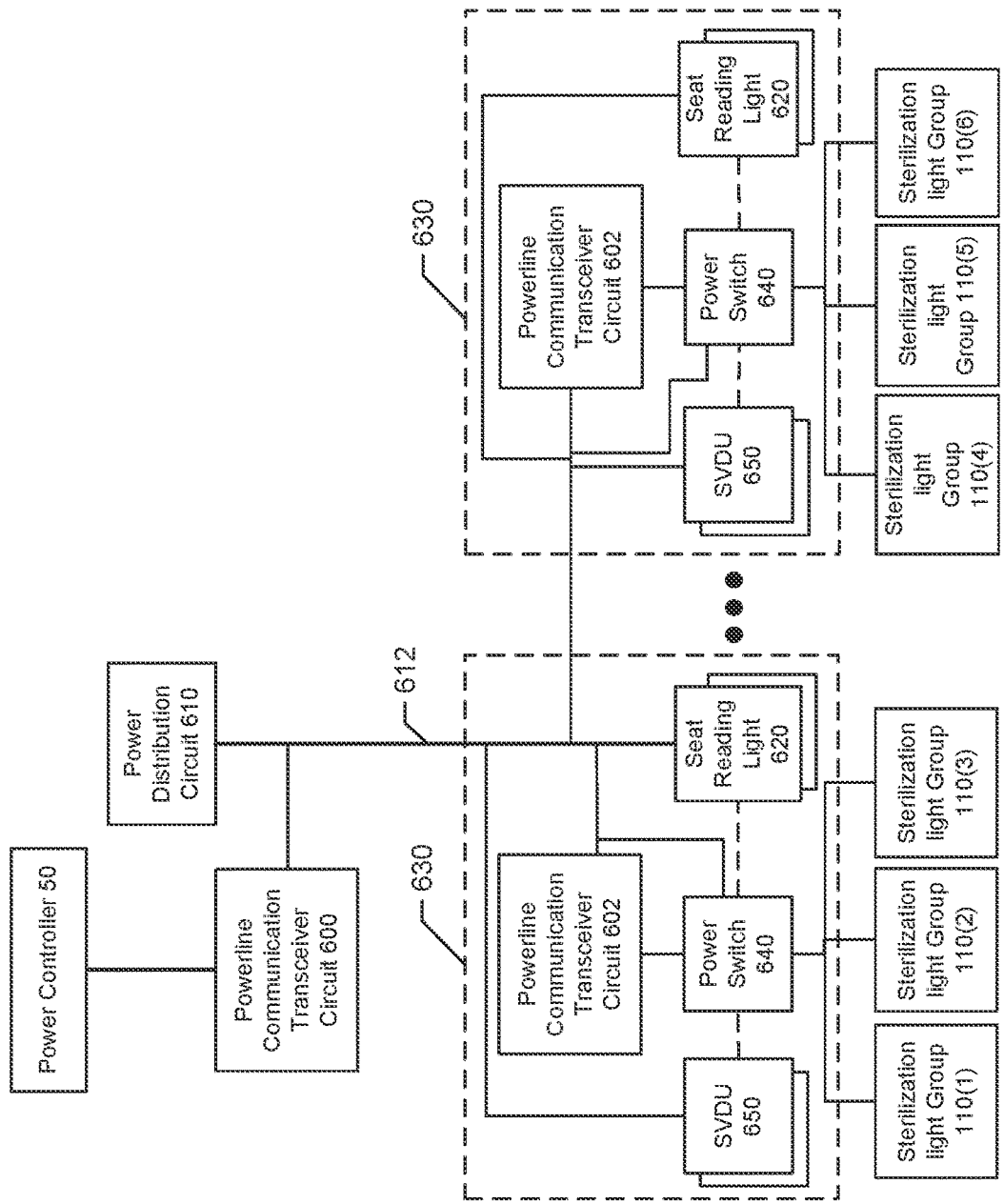
FIG. 5 is a block diagram that is configured with powerline communication transceiver circuits that communicate group selection commands through powerlines supplying power to sterilization lights, in accordance with some embodiments of the present disclosure.

FIG. 5 is a block diagram of a power system that is configured with powerline communication transceiver circuits 600 that communicate group selection commands through powerlines supplying power to sterilization lights.

In some embodiments, the pathogen sterilization light assembly includes the power system of FIG. 5.

The power system may include a power supply (e.g., power supply 20 of FIG. 1) that is connected to a power distribution circuit 610 that supplies power through powerlines 612 (e.g., low voltage powerlines) to seat reading light devices 620, SVDUs 650, and/or to supply power to other seat electronic devices that are distributed within the vehicle.

The power system may further include a power controller 50 and powerline communication transceiver circuits 600/602. The powerline communication transceiver circuits 600/602 may be configured to send and receive data through the powerlines 612.

In some embodiments, the sterilization lights are divided into groups (e.g., sterilization light groups 110(1)-(6)). The pathogen sterilization light assembly further includes the power controller 50 and power switches 640 which are connected to allow power distribution from a power supply and cease power distribution from the power supply to different ones of the groups of the sterilization lights. The power controller 50 is configured to separately control the power switches 640 to control which of the groups of the sterilization lights is powered at a time by the power supply.

In some embodiments, a number of the sterilization lights in the groups is defined based on at least one of: a maximum power distribution of powerlines extending through the cabin to power the sterilization lights in the group; and a maximum power supply rating of the power source supplying power to the power switches for distribution.

In some embodiments, the power controller 50 is configured to activate (through the powerline communication transceiver circuit 600) the power supply to provide power to a group 110(1)-(6) of the sterilization lights. The activation is based on signaling from at least one proximity sensor indicating no person are in the area. The power controller 50 may also be configured to deactivate (through the powerline communication transceiver circuit 600) the power supply to cease providing power to the group 110(1)-(6) of the sterilization lights. The deactivation may be based on the at least one proximity sensor indicating a person has entered the area.

In some embodiments, the deactivation is based on a measured or predefined dosage being met. For example, the intensity of a group 110(1) (or a sterilization light) may be measured or predefined and the duration that the group 110(1) (or a sterilization light) is activated for may be measured. The intensity and duration may be sent to the power controller 50 (through the powerline communication transceiver circuits 600/602) and the power controller 50 may determine the dosage that the group 110(1) has produced. Once the produced dosage is greater than or equal to a threshold value, the power controller 50 may deactivate the group 110(1) and activate another group 110(2).

As explained above, the power-on time controlled by the controller 50 for a sterilization light or a group of sterilization lights may be determined based on an estimated time that the aircraft will remain on the ground between flights and/or based on a determination of how many times and/or how long a seat has been occupied since a last sterilization process has been performed. Moreover, as explained above, the controller 50 may control a motor to angularly rotate a sterilization light to sequentially expose, e.g. statically exposed or angularly scan, a UV light beam toward a plurality of different seat areas that are selected based on an estimated time that the aircraft will remain on the ground between flights and/or based on a determination of how many times and/or how long a seat has been occupied since a last sterilization process has been performed.

In some embodiments, the power system includes a plurality of powerline communication transceiver circuits 602 connected to powerlines 612 connected to feed power from the power supply to the groups 110(1)-(6) of sterilization lights. The plurality of powerline communication transceiver circuits 602 are spaced apart in the cabin and each connected to one of the power switches 640. The power controller 50 communicates group selection commands through the powerline communication transceiver circuits 602 and the powerlines 612 to control switching of the power switches 604. The power controller 50 may communicate motor control commands, which motor(s) are used to select and rotate one or more of the sterilization lights, through the powerline communication transceiver circuits 602 and the powerlines 612 to control selection and rotation of the motor(s).

Powerline communication is thereby used in FIG. 5 to communicate the group selection commands from the power controller 50 to the power switch 640.

In some embodiments, the powerline communication transceiver circuit 600 may superimpose low-energy information signals onto power waveforms of the powerlines 612. The low-energy information signals can be modulated to communicate the group selection commands generated by power controller.

This approach, using powerline communications, can avoid the need to install dedicated command (digital data) communication networks to the power controller 50 and enables the typical low-voltage powerlines which are installed to seat areas to also transport both power for the sterilization lights and commands that control switching between power-on and power-off and/or angular rotation of individually selected (commands that control individually addressed) sterilization lights or selected group(s) of sterilization lights. Sending the group selection commands through the powerlines avoids burdening other aircraft data networks, avoids the need for installation of dedicated data communication networks for controlling sterilization lights, and/or avoids the need for inclusion of wireless transceiver circuits connected to the sterilization lights and associated RF interference generated within the cabin if the group selection commands were to be transmitted through wireless communication networks.

The power system may further include a power switch 640 that is configured to be controlled through group selection commands from the power controller 50. Based on the group selection commands, the power switch 640 switches which group of sterilization lights receive power, i.e., turn-on, and/or control angular rotation of sterilization lights by motors. Additionally, the power switch may control if the seat reading light devices 620, the SVDUs 650, and other seat electronic devices receive power distribution through the group selection commands. For example, if the power controller 50 sends group selection commands through the powerline communication transceiver circuit 600 to the powerline communication transceiver circuit 602 and to the power switch 640 then the power switch may deactivate the power distribution to the seat reading light devices 620, the SVDUs 650, and other seat electronic devices.

Vehicles such as, for example, aircraft can have relatively low constraints on the maximum power supply rating for an installed powerlines and through which a power supply can supply power to seat reading light devices 620, SVDUs 650, and other seat electronic devices. By dividing sterilization lights into groups and then sequentially, or otherwise, activating/deactivating groups of sterilization lights, this can be configured to ensure the power distribution requirements of the power supply are kept below a defined maximum maximum power supply rating and/or the power distributed through the powerlines is kept below a defined power rating.

In some embodiments, the power switch 640 is connected to the seat reading light devices 620, the SVDUs 650, and other seat electronic devices such that the power switch 640 and configured to switch power distribution alternately between one or more of the seat reading light devices 620, the SVDUs 650, and other seat electronic devices to the sterilization light groups 110(1)-(6).

In some embodiments, the seat reading light devices 620, the SVDUs 650, and other seat electronic devices are powered directly be the power distribution circuit 610 through the powerlines 612.

In some embodiments, the group selection commands provided by the power controller 50 include an activation group identifier that indicates which of the power switches is to be activated to allow power distribution and/or a deactivation group identifier which indicates which of the power switches is to be deactivated to cease power distribution.

In some embodiments, the group selection command separately controls switching of single switched groups 630 containing any defined numbers of sterilization light groups in the vehicle. For example, in FIG. 5, the switched groups 630 is structurally defined to enable switching (e.g., power switching and/or angular rotational movement switching) of three sterilization light groups through the power switch 640.

In some embodiments, the pathogen sterilization light assembly includes a power system similar to FIG. 5, however does not send the group selection commands through a powerline communication transceiver circuit and through powerlines but rather through a shared or dedicated wired network (e.g., Ethernet, etc.) or wireless network (e.g., WiFi, Bluetooth, etc.).

In some embodiments, the power controller 50 selects an activation group identifier, from a list of activation group identifiers, that triggers emission of UV light from sterilization lights associated with activation group identifier toward a prioritized passenger seat or row of passenger seats during a sterilization procedure. The selection can be based on flight information that includes at least one of: a duration of time between passenger deboarding at the end of a flight and passenger boarding for a next flight; a seating assignment that indicates which passenger seats or rows of passenger seats were occupied on a previous flight; and a seating assignment that indicates which passenger seats or rows of passenger seats are assigned to be occupied on a next flight. For example, the controller 50 may obtain a seat assignment manifest for a previously completed flight and/or for a next flight and cause a UV light sterilization process to be selectively performed on only the seats that are identified from the seat assignment manifest as having been occupied on a previous flight and/or which are assigned to be occupied on a next flight. As explained above, the selection of which seats will be exposed to UV light and the duration of exposure may be determined based on which seats were occupied and/or for how long those seats were occupied.

For example, if flight information indicates that passengers are seated in every other row of passenger seats, such that there is an empty row of passenger seats between each occupied row of passenger seats, then the power controller 50 may select activation group identifiers of the groups of sterilization lights that direct UV light toward rows of passenger seats that are to be occupied. In this instance, the rows of passenger seats that are to be occupied are the prioritized row of passenger seats for the UV light sterilization process.

In some embodiments, the power controller 50 selects an activation group identifier from a list of activation group identifiers that direct UV light toward a prioritized passenger seating surface. The selection is based on flight information that includes at least one of a duration of time between between passenger deboarding and passenger boarding and a seating assignment that indicates which passenger seat or rows of passenger seats are to be occupied.

When the time duration satisfies a defined rule prioritizing speed, certain passenger seating areas can be prioritized for UV light exposure such as according to the process described above.

For example, if flight information indicates that is a short duration of time between when an aircraft is to be deboarded and boarded, the power controller 50 can respond by operationally selecting activation group identifiers of the groups of sterilization lights that direct UV light toward prioritized passenger seating surfaces such as headrest surfaces and armrest surfaces.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A pathogen sterilization light assembly for a vehicle cabin, comprising:
    a plurality of sterilization lights mounted at spaced apart locations along a cabin of the vehicle and configured to emit ultraviolet light directed toward areas within the cabin to sterilize pathogens; and
    a power controller configured to:
        control which of the sterilization lights is powered by a power supply at a time, and
        select which of the sterilization lights are powered on at a time based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

2. The pathogen sterilization light assembly of claim 1, wherein the sterilizing lights are at least one of short-wave ultraviolet lamps, ultraviolet light emitting diodes, ultraviolet lasers, and vacuum ultraviolet devices.

3. The pathogen sterilization light assembly of claim 1, wherein the sterilization lights are configured to be at least partially integrated within a ceiling above a passenger seat within the cabin, and powered by powerlines extending along the ceiling.

4. The pathogen sterilization light assembly of claim 3, wherein one of the sterilization lights is mounted to direct ultraviolet light toward at least one of: a passenger seat, a row of passenger seats, and an isle and a plurality of passenger seats within the vehicle.

5. The pathogen sterilization light assembly of claim 3, wherein one of the sterilization lights is connected to a rotational motor configured to rotate the sterilization light to scan a focused beam of ultraviolet light along passenger seating surfaces of at least one passenger seat.

6. The pathogen sterilization light assembly of claim 1, wherein the sterilization lights are configured to be at least partially integrated within a back surface of passenger seats within the cabin and powered by powerlines extending within the passenger seats.

7. The pathogen sterilization light assembly of claim 6, wherein the sterilization lights are connected to receive power being supplied to seatback video display unit circuits within the passenger seats.

8. The pathogen sterilization light assembly of claim 6, wherein one of the sterilization light is integrated in the back surface of one of the passenger seats and configured to direct ultraviolet light toward passenger seating surfaces of another one of the passenger seats located behind the passenger seat and toward a tray mounted to the back surface of the passenger seat.

9. The pathogen sterilization light assembly of claim 8, wherein one of the sterilization lights is connected to a rotational motor configured to rotate the sterilization light relative to the passenger seat to scan a focused beam of ultraviolet light along the passenger seating surfaces of the other one of the passenger seats located behind the passenger seat.

10. The pathogen sterilization light assembly of claim 1, wherein the sterilization lights are configured to be at least partially integrated within a wall of the cabin to direct ultraviolet light toward a row of passenger seats, and powered by powerlines extending along the wall.

11. The pathogen sterilization light assembly of claim 1, wherein one of the sterilization lights is partially integrated within at least one of: a bottom surface of a tray extendable from a passenger seat to direct ultraviolet light toward a passenger seating surface of another passenger seat located behind the passenger seat while the tray is stored in an upright position; and an end surface of the tray to direct ultraviolet light toward the passenger seating surface of the other passenger seat located behind the passenger seat while the tray is deployed in a down position, and the sterilization light is powered by powerlines extending through the passenger seat and the tray.

12. The pathogen sterilization light assembly of claim 1, wherein the power controller is further configured to:
supply power to the sterilization lights based on signaling from at least one proximity sensor indicating no person is present; and
cease supply of power to the sterilization lights based on the at least one proximity sensor indicating a person has become present.

13. The pathogen sterilization light assembly of claim 1, wherein the power controller is further configured to:
control duration of power supplied to which of the sterilization lights based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

14. A pathogen sterilization light assembly for a vehicle cabin, comprising:
a plurality of sterilization lights mounted at spaced apart locations along a cabin of the vehicle and configured to emit ultraviolet light directed toward areas within the cabin to sterilize pathogens, wherein the sterilization lights are divided into groups;
a power controller and power switches which are connected to alternate between allowing power distribution from a power supply and ceasing power distribution from the power supply to different ones of the groups of the sterilization lights, wherein the power controller is configured to separately control the power switches to select which of the groups of the sterilization lights is powered by the power supply at a time;
wherein a number of the sterilization lights in the groups which is connected through a same one of the power switches is defined based on at least one of: a maximum power distribution of powerlines extending through the cabin to power the sterilization lights in the group and a maximum power supply rating of a power source supplying power to the power switches for distribution; and
the power controller is configured to separately control the power switches to not power-on more than one of the groups of the sterilization lights a time.

15. The pathogen sterilization light assembly of claim 14, further comprising:
a plurality of WiFi transceivers each connected to one of the power switches,
wherein the power controller provides group selection commands to a wireless access point for transmission to the WiFi transceivers connected to the power switches to control switching of the power switches.

16. The pathogen sterilization light assembly of claim 14, wherein the power controller selects a group of the power switches to power-on to supply power to the sterilization lights which direct UV light toward a prioritized passenger seat or row of passenger seats, based on flight information that includes at least one of: a duration of time between passenger deboarding and passenger boarding; a seating assignment that indicates which passenger seat or rows of passenger seats have been occupied on a previous flight; and seating assignment that indicates which passenger seat or rows of passenger seats are assigned to be occupied on a next flight.

17. A pathogen sterilization light assembly for a vehicle cabin, comprising:
a plurality of sterilization lights mounted at spaced apart locations along a cabin of the vehicle and configured to emit ultraviolet light directed toward areas within the cabin to sterilize pathogens, wherein the sterilization lights are divided into groups;
a power controller and power switches which are connected to alternate between allowing power distribution from a power supply and ceasing power distribution from the power supply to different ones of the groups of the sterilization lights, wherein the power controller is configured to separately control the power switches to select which of the groups of the sterilization lights is powered by the power supply at a time; and
a plurality of powerline communication transceiver circuits connected to powerlines connected to supply power from the power supply to the groups of sterilization lights,
wherein the plurality of powerline communication transceiver circuits are spaced apart in the cabin and each connected to one of the power switches, and
wherein the power controller communicates group selection commands through the powerline communication transceiver circuits and the powerlines to control switching of the power switches.

18. The pathogen sterilization light assembly of claim 17, wherein the power controller provides group selection commands that include an activation group identifier that indicates which of the power switches is to be activated to allow power distribution and/or a deactivation group identifier which indicates which of the power switches is to be deactivated to cease power distribution.

19. The pathogen sterilization light assembly of claim 17, wherein each of the powerline communication transceiver circuits is configured to superimpose low-energy information signals onto power waveforms of the powerlines, the low-energy information signals being modulated to communicate the group selection commands.

20. A pathogen sterilization light assembly for a vehicle cabin, comprising:
- a plurality of sterilization lights mounted at spaced apart locations along a cabin of the vehicle and configured to emit ultraviolet light directed toward areas within the cabin to sterilize pathogens; and
- a power controller configured to select a group of the sterilization lights to be powered-on during a sterilization procedure based on flight information that includes at least one of: a duration of time between passenger deboarding at an end of a flight and passenger boarding for a next flight; a seating assignment that indicates which passenger seats or rows of passenger seats were occupied on a previous flight; and a seating assignment that indicates which passenger seats or rows of passenger seats are to be occupied on a next flight, and to control initiation and cessation of supply of power to the selected group of the sterilization light.

21. The pathogen sterilization light assembly of claim 20, wherein the power controller is further configured to:
- supply power to the group of the sterilization lights based on signaling from at least one proximity sensor indicating no person is present; and
- cease supply of power to the group of the sterilization lights based on the at least one proximity sensor indicating a person has become present.

22. The pathogen sterilization light assembly of claim 20, wherein the sterilizing lights are at least one of short-wave ultraviolet lamps, ultraviolet light emitting diodes, ultraviolet lasers, and vacuum ultraviolet devices.

23. A pathogen sterilization light assembly for a vehicle cabin, comprising:
- a plurality of sterilization lights mounted at spaced apart locations along a cabin of the vehicle and configured to emit ultraviolet light directed toward areas within the cabin to sterilize pathogens;
- a rotational motor configured to rotate at least one of the sterilization lights relative to at least one passenger seat to scan a focused beam of ultraviolet light along surfaces of the at least one passenger seat; and
- a controller connected to control the rotational motor to control angular rotation, range of rotation, and/or rate of angular rotation of the at least one sterilization light based on information indicating at least one of: whether the at least one passenger seat has been occupied on a previous flight; whether the at least one passenger seat is assigned to be occupied on a next flight; how many times the at least one passenger seat has been occupied on previous flights since a last sterilization process has been performed; and/or a total time duration the at least one passenger seat has been occupied on one or more previous flights since a last sterilization process has been performed.

24. The pathogen sterilization light assembly of claim 23, wherein the controller is further configured to define a set of areas of a seating surface to be sterilized, and to control the rotational motor to incrementally step a focused beam of UV light of one of the at least one of the sterilization lights from being directed toward a first area in the set in which a sterilization process has been performed to become directed at a second area in the set to initiate the sterilization process the second area while rapidly skipping over an intervening area between the first and second areas without performing the sterilization process in the intervening area.

25. The pathogen sterilization light assembly of claim 24, wherein:
- the controller is configured to define a number of areas in the set to incrementally step the at least one of the sterilization lights between to perform the sterilization process on based on information indicating at least one of: locations of passenger seats that have been occupied on a previous flight; locations of passenger seats that are assigned to be occupied on a next flight; locations of passenger seats that have been occupied at least a threshold number of times on previous flights since a last sterilization process has been performed; and/or locations of passenger seats that have been occupied at least a threshold total time on one or more previous flights since a last sterilization process has been performed.

* * * * *